Jan. 30, 1940. C. SALBACH Plant Pat. 356
GLADIOLUS
Filed March 20, 1939
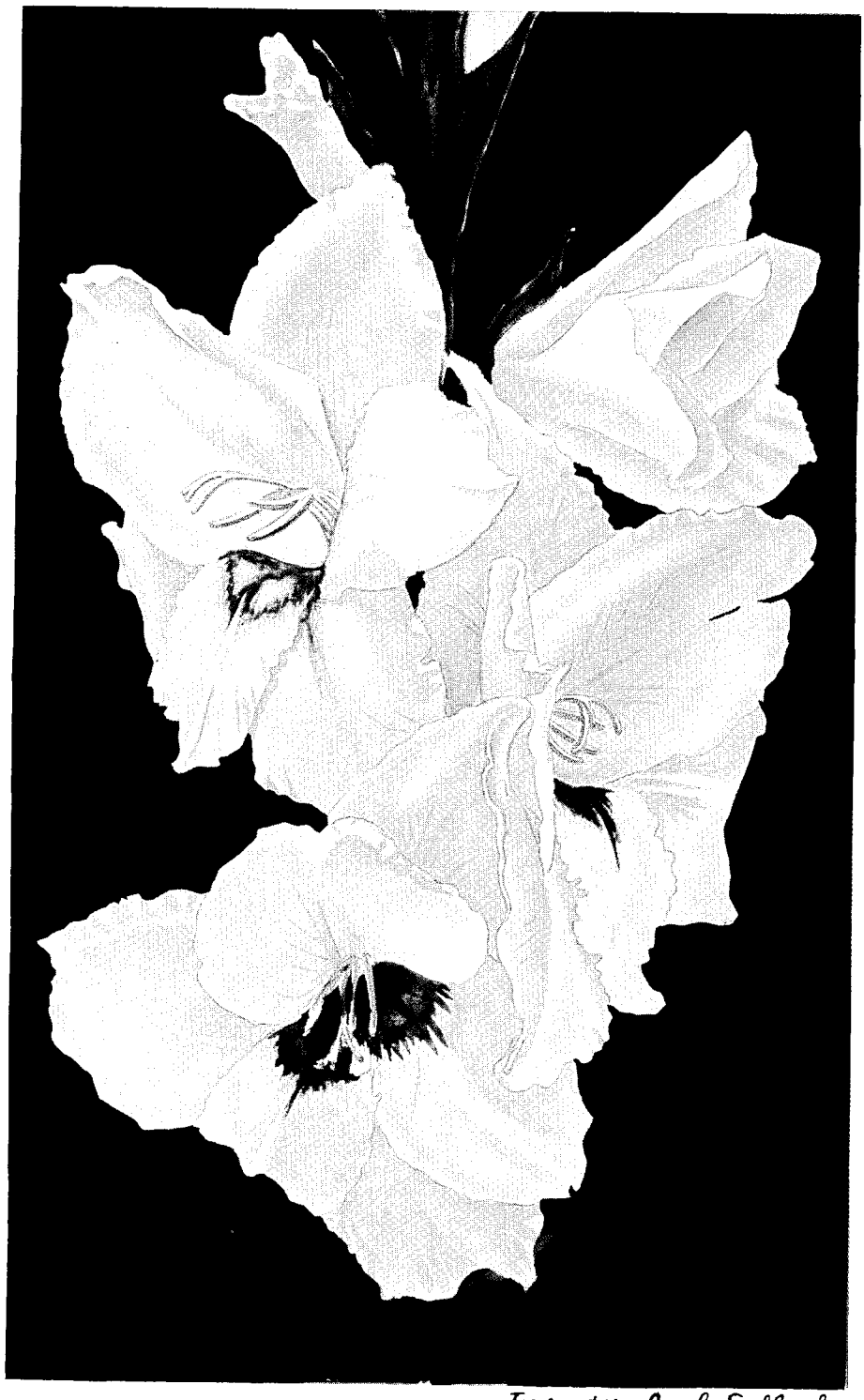
Inventor-Carl Salbach
By Orville M. Kile - Plant Pat. Agent Patented Jan. 30, 1940

Plant Pat. 356

UNITED STATES PATENT OFFICE

356

GLADIOLUS

Carl Salbach, Contra Costa County, Calif., assignor to Ella S. Salbach, Contra Costa County, Calif.

Application March 20, 1939, Serial No. 262,984

1 Claim. (Cl. 47—60)

My present invention relates to improvements in flowering gladioli of the type notable for size and quality of bloom. The object of this invention is to provide a superior gladiolus of white to ivory yellow color, with carmine blotch, and to provide such gladiolus with very large individual flowers of good quality which are unusually well placed and well formed.

My new variety originated as a seedling produced from cross pollination work carried on by myself, and is a cross between two unnamed seedlings which in turn had been produced by a cross of Picardy and Senorita for the seed parent and two unnamed seedlings for the pollen parent. This new variety has been asexually reproduced through several generations and its characteristics appear to be permanently fixed.

The illustration accompanying this specification shows a portion of a spike of this variety in approximately its true colors but somewhat reduced.

Color plate references are to Ridgway's Color Standards and Nomenclature.

Following is a more complete description of the plant and flower of this new variety of gladiolus.

*The plant*

Growth:

Very vigorous although not exceptionally tall, the tips of its spikes ordinarily reaching a height of about 38 inches in my gardens.

Blooming:

Usually each spike opens five to six of its very large flowers at one time, and has a total of sixteen to eighteen flowers in all.

Arrangement:

Flowers symmetrically placed and facing in one direction. This is a consistent achievement of my new variety.

Foliage:

Moderately heavy in quantity (usually seven leaves). Peacock Green (Plate VI). About 12 inches in length. Slightly drooping.

Stems:

Strong, stiff and straight. Fully adequate to hold the heavy flower spike.

Corms:

Larger than average. White and flat.

*The flower*

The blossom:

*Size.*—Lower blossoms usually six inches across, sometimes slightly larger. Much larger than flowers of other varieties of similar color grown under same conditions.

*Form.*—Usually nearly round, giving the flower an apparent size that is greater than indicated by measurements of width.

*Petals.*—Smooth in the center, with one or two flutings running from the center to the edge of the flower, but the edges of the petals have many tiny pleat-like wrinkles which give the flower a small but definite ruffling at the edge.

*Substance.*—Heavy, thus making the variety very valuable for shipping and long keeping.

*Color.*—Between White and Ivory Yellow (Plate XXX), with a double blotch in the center of the flower. The inner blotch is usually diamond shaped and Carmine (Plate I) in color. It is overlaid on the outer blotch which is Buff Yellow (Plate IV). The colors are clear and distinct and the contrast very definite.

*Stamens.*—The three stamens are between White and Ivory Yellow (Plate XXX), with anthers of the same color on top and slightly darker underneath.

*Pistils.*—Slender. Unusually long. Between White and Ivory Yellow (Plate XXX).

*Comparison*

Other known varieties of similar color have much smaller flowers. The closest approach to my new variety is the gladiolus Mme. Sully, which differs in many respects, particularly in that it is shorter and its flowers are much less than half the size of those of my new variety.

The most notable characteristics which in combination distinguish my new gladiolus from all other similarly colored varieties, are:

1. The great size of the flowers.
2. The round form of the flowers, which emphasizes its apparent size.
3. The general good form of the flower and the consistency of the variety in its production of spikes of good form and habit.
4. The general symmetry and placement of the flowers.
5. The heavy substance of the petals and the resultant good keeping quality.
6. The clarity of the color, and the contrasting emphasis from the color of the blotch.

Having thus disclosed my invention, I claim:

The new variety of gladiolus plant herein described and illustrated, characterized by its consistency of good growth and form of spike, and its flowers of great size, heavy substance, and striking blotched coloring as described.

CARL SALBACH.